United States Patent [19]

Cashin et al.

[11] Patent Number: 4,612,324
[45] Date of Patent: Sep. 16, 1986

[54] IMIDAZOLE DERIVATIVES FOR TREATING JOINT DISEASES AND WILSON'S DISEASE

[75] Inventors: Colin H. Cashin, Preston near Hitchin; Noel A. Roberts; Brian P. Tong, both of Harpenden, all of Great Britain

[73] Assignee: Hoffmann-La Roche Inc., Nutley, N.J.

[21] Appl. No.: 576,083

[22] Filed: Feb. 1, 1984

[30] Foreign Application Priority Data

Feb. 15, 1983 [GB] United Kingdom ............... 8304182
Nov. 2, 1983 [GB] United Kingdom ............... 8329238

[51] Int. Cl.4 ........................................... A61K 31/415
[52] U.S. Cl. .................... 514/400; 548/342; 548/344
[58] Field of Search ............... 548/342, 344; 424/273 R; 514/400

[56] References Cited

U.S. PATENT DOCUMENTS 2,616,828 11/1952 Levinton et al. ............... 548/344 X
3,855,238 12/1974 Batesky et al. ............... 548/344 X

FOREIGN PATENT DOCUMENTS 698066 11/1964 Canada ............................. 548/344

OTHER PUBLICATIONS

*Chemical Abstracts,* 78:53224t (1973) [Trout, G., *J. Med. Chem.,* 1972, 15(12), 1259–1261].
*Chemical Abstracts,* 73:31819k (1970) [Gonchar, N., et al., *Biokhimiya* 1970, 35(2), 224–8].
*Chemical Abstracts,* 74:100398g (1971) [Felix, A., et al., *Org. Prep. Proced.* 1970, 2(4), 255–8].
Trout, G., *J. Med. Chem.,* 1972, 15(12), 1259–61.
Jones, R., *J. Am. Chem. Soc.,* 71, 383(1949).
Hsien, K., et al., *J. Med. Chem.,* 1979, 22(10), 1199–1206.
*Chemical Abstracts,* 57:5403e Schneider, F., et al., *Z. Physiol. Chem.,* 327, 74–85 (1962).

*Primary Examiner*—Richard A. Schwartz
*Attorney, Agent, or Firm*—Jon S. Saxe; Bernard S. Leon; Matthew Boxer

[57] ABSTRACT

Compounds of the formula

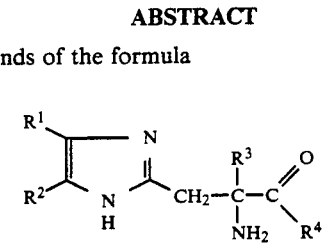

wherein $R^1$, $R^2$ and $R^3$ each individually is hydrogen, or lower alkyl and $R^4$ is hydroxy, lower alkoxy, aryl(lower alkoxy), amino, mono(lower alkyl)amino or di(lower alkyl) amino, and pharmaceutically acceptable salts thereof which are useful in the treatment of degenerative joint diseases and of Wilson's disease are described.

3 Claims, No Drawings

IMIDAZOLE DERIVATIVES FOR TREATING JOINT DISEASES AND WILSON'S DISEASE

BRIEF SUMMARY OF THE INVENTION

The invention is concerned with imidazole derivatives and pharmaceutical compositions containing said imidazole derivatives.

The pharmaceutical preparations provided by the invention contain as an essential active ingredient a D,L-, D- or L-compound of the formula

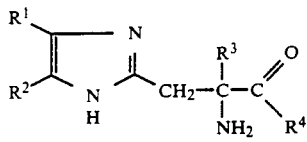

wherein $R^1$, $R^2$ and $R^3$ each individually is hydrogen or lower alkyl and $R^4$ is hydroxy, lower alkoxy, aryl-(lower alkoxy), amino, mono(lower alkyl)amino or di(lower alkyl)amino,
or a pharmaceutically acceptable salt thereof.

The pharmaceutical preparations provided by the invention are useful in the treatment of degenerative joint diseases such as rheumatoid arthritis and osteoarthritis as well as of Wilson's disease.

The invention also relates to processes for preparing imidazole derivatives. The invention also relates to methods for using imidazole derivatives in the treatment of degenerative joint diseases such as rheumatoid arthritis and osteoarthritis as well as Wilson's disease.

DETAILED DESCRIPTION OF THE INVENTION

As used in this specification, the term "lower alkyl", alone or in combination such as in "mono(lower alkyl)amino" and "di(lower alkyl)amino" means a straight-chain or branched-chain alkyl group which contains up to 4 carbon atoms such as methyl, ethyl, n-propyl, isopropyl, n-butyl and tert.butyl. The term "lower alkoxy" means a straight-chain or branched-chain alkoxy group which contains up to 4 carbon atoms such as methoxy, ethoxy, n-propoxy, isopropoxy, n-butoxy and tert.butoxy. The term "aryl-(lower alkoxy)" means a lower alkoxy group in which one of the hydrogen atoms has been replaced by unsubstituted phenyl or phenyl carrying one or more substituents selected from, for example, lower alkyl, lower alkoxy and halogen, examples of such aryl-(lower alkoxy) groups being benzyloxy, 2-phenylethoxy and the like. Methylamino, ethylamino and the like are examples of mono-(lower alkyl)amino groups and dimethylamino, diethylamino, ethylmethylamino and the like are examples of di(lower alkyl)amino groups. The term "halogen" means fluorine, chloride, bromine or iodine.

The pharmaceutically acceptable salts of the compounds of formula I can be salts formed with pharmaceutically acceptable inorganic acids, for example, hydrohalic acids, such as hydrochloric acid, hydrobromic acid and hydroiodic acid and the like; nitric acid, phosphoric acid and the like; and with pharmaceutically acceptable organic acids, for example, acetic acid, tartaric acid, citric acid, fumaric acid, maleic acid, malic acid, methanesulfonic acid, p-toluenesulfonic acid and the like. These pharmaceutically acceptable acid addition salts can be mono-salts or di-salts. Compounds of formula I in which $R^4$ is hydroxy can also form pharmaceutically acceptable salts with pharmaceutically acceptable bases, examples of such salts being alkali metal salts such as the sodium salt and the potassium salt, alkaline earth metal salts such as the calcium salt, the ammonium salt and the like.

The compounds of formula I contain an asymmetric carbon atom and can exist in racemic or optically active form. Formula I is accordingly intended to embrace the racemic mixture, that is D,L-enantiomers and the optically active D-enantiomer and L-enantiomers.

Preferred pharmaceutical preparations provided by the present invention contain a compound of formula I in which $R^1$, $R^2$ and $R^3$ each is hydrogen and $R^4$ is lower alkoxy, especially ethoxy, or a pharmaceutically acceptable salt thereof. Especially preferred pharmaceutical preparations provided by the present invention contain ethyl D-α-amino-2-imidazolepropionate or a pharmaceutically acceptable salt thereof.

Examples of other pharmaceutical preparations provided by the present invention are those which contain one of the following compounds of formula I or a pharmaceutically acceptable salt thereof:
D,L-α-amino-2-imidazolepropionic acid,
D-α-amino-2-imidazolepropionic acid,
L-α-amino-2-imidazolepropionic acid,
methyl D,L-α-amino-2-imidazolepropionate,
methyl L-α-amino-2-imidazolepropionate,
methyl D-α-amino-2-imidazolepropionate,
ethyl D,L-α-amino-2-imidazolepropionate,
ethyl L-α-amino-2-imidazolepropionate,
benzyl D,L-α-amino-2-imidazolepropionate,
benzyl D-α-amino-2-imidazolepropionate,
benzyl L-α-amino-2-imidazolepropionate,
D,L-α-amino-α-methyl-2-imidazolepropionic acid,
D,L-α-amino-4,5-dimethyl-2-imidazolepropionic acid,
D,L-α-amino-2-imidazolepropionamide,
D,L-α-amino-N-methyl-2-imidazolepropionamide and
D,L-α-amino-N,N-dimethyl-2-imdazolepropionamide.

The pharmaceutical compositions provided by the invention are useful in the treatment of degenerative joint diseases such as rheumatoid arthritis and osteoarthritis as well as of Wilson's disease.

The pharmaceutical preparations provided by the present invention can be administered orally, for example, in the form of tablets, dragées, hard gelatine capsules, soft gelatine capsules, solutions, emulsions or suspensions or parenterally, for example, in the form of injection solutions.

The carrier material present in the pharmaceutical preparations provided by the present invention can be a pharmaceutically inert, inorganic or organic carrier. Examples of such carriers which can be used for tablets, dragées and hard gelatine capsules are lactose, maize starch or derivatives thereof, talc, stearic acid or its salts and the like. Examples of suitable carriers for soft gelatine capsules are vegetable oils, waxes, fats, semi-solid and liquid polyols and the like. Suitable carriers for the production of solutions and syrups include, for example, water, polyols, saccharose, invert sugar, glucose and the like. Suitable carriers for injection solutions are, for example, water, alcohols, polyols, glycerine, vegetable oils and the like.

The pharmaceutical preparations provided by the present invention can also contain preserving agents, solublizing agents, stabilizing agents, wetting agents, emulsifying agents, sweetening agents, colouring agents, flavouring agents, salts for varying the osmotic pressure, buffers, coating agents or antioxidants. The present pharmaceutical preparations can contain other therapeutically valuable substances in addition to the compounds of formula I and their pharmaceutically acceptable salts.

The pharmaceutical preparations provided by the invention can be manufactured by mixing a compound of formula I or a pharmaceutically acceptable acid addition salt thereof and, if desired, one or more other therapeutically valuable substances with a pharmaceutical carrier material and bringing the mixture into a galenical administration form.

Appropriate pharmaceutical dosage forms provided by the invention contain from about 125 mg to about 400 mg of a compound of formula I or a pharmaceutically acceptable salt thereof depending on the particular dosage form and compound or salt used.

The dosage of a compound of formula I or a pharmaceutically acceptable salt thereof to be administered varies according to the particular compound or salt in question, the particular condition under treatment as well as the needs and requirements of the patient as determined by the attending physician. For example, the compounds of formula I and their pharmaceutically acceptable salts can be administered in a daily dosage from about 250 mg to about 1500 mg in the treatment of degenerative joint diseases and in a daily dosage of up to about 3 g in the treatment of Wilson's disease. It will be appreciated that this dosage is given by way of example only and can be varied upwards or downwards.

The pharmacological activity of the compounds of formula I can be demonstrated in the following tests:

(i) IN VITRO TEST FOR SUPEROXIDE DISMUTASE-LIKE ACTIVITY AND THE STABILITY OF COPPER CHELATES OF COMPOUNDS OF FORMULA I

Solutions of copper, as copper (II) bisglycinate, and test compound were prepared at concentrations of $10^{-2}M$. The copper and test compound in the molar ratio of 1:4 were then diluted in 100 mM Hepes buffer, pH 7.8, to a final copper concentration of $10^{-3}M$. This solution was further diluted tenfold in buffer, mixed in varying known proportions with ethylenediaminetetraacetic acid and the mixture was left to equilibrate at room temperature for 1 hour. Aliquots calculated to give a final ethylenediaminetetraacetic acid concentration of 20 μM were taken and tested as follows for the inhibition of the reduction of nitroblue tetrazolium by the superoxide radical.

The assay solution contained $2 \times 10^{-5}M$ hypoxanthine, $5 \times 10^{-4}M$ nitroblue tetrazolium, 1 mg/ml gelatine and 100 mM Hepes buffer, pH 7.8, to a total assay volume of 3.0 ml. The reaction was initiated by the addition of 30 μl of 0.1 units/ml xanthine oxidase and allowed to go to completion at room temperature, usually overnight. The reduction of nitroblue tetrazolium was measured photometrically at 550 nm.

The presence of superoxide dismutase-like activity inhibits the reduction of nitroblue tetrazolium and the concentration of copper required for 50% inhibition ($I_{50}$) can be determined, maintaining the ethylenediaminetetraacetic acid concentration at 20 μM.

The results obtained in the above test are compiled in Table I:

TABLE 1

| Test Compound | $I_{50}$ μM |
| --- | --- |
| D,L-α-amino-2-imidazolepropionic acid | 3.5 |
| L-α-amino-2-imidazolepropionic acid | 3.5 |
| D-α-amino-2-imidazolepropionic acid | 3.5 |
| Methyl D,L-α-amino-2-imidazolepropionate | 2.5 |
| Methyl D-α-amino-2-imidazolepropionate | 3.0 |
| Methyl L-α-amino-2-imidazolepropionate | 3.0 |
| Ethyl D,L-α-amino-2-imidazolepropionate | 2.5 |
| Ethyl D-α-amino-2-imidazolepropionate | 2.5 |
| Ethyl L-α-amino-2-imidazolepropionate | 2.5 |
| Benzyl D,L-α-amino-2-imidazolepropionate | 2.0 |
| Benzyl D-α-amino-2-imidazolepropionate | 2.0 |
| Benzyl L-α-amino-2-imidazolepropionate | 2.0 |
| D,L-α-amino-α-methyl-2-imidazolepropionic acid | 3.0 |
| D,L-α-amino-4,5-dimethyl-2-imidazolepropionic acid | 8.5 |
| D,L-α-amino-2-imidazolepropionamide | 3.0 |
| D,L-α-amino-N—methyl-2-imidazolepropionamide | 3.5 |
| D,L-α-amino-N,N—dimethyl-2-imidazolepropionamide | 3.5 |

(ii) IN VIVO CUPRIURESIS TEST

The test method, which was based on that of K. Gibbs and J. M. Walshe (Clin. Sc. Mol. Med., 53, 317-320, 1977), was carried out as follows:

Male rats weighing 120-200 g were starved on the morning of the test day. The rats were dosed orally (10 ml/kg) in groups of four late in the afternoon of the test day and then housed individually in metabolic cages for 18 hours. During this period urine was collected separately from feces. The rats had access to deionized water ad libitum and to a 10 g food pellet made up from powdered rat diet bound with arachis oil and tragacanth plus Tween 80* in distilled water. At 18 hours the urine volume of each rat was recorded and the copper concentration was determined using atomic absorption spectrophotometry at 324 nm. Copper excretion was expressed in μmol Cu.kg$^{-1}$ and percentage changes from controls were calculated using the following equation:

$$\frac{(Test - Control)}{Control} \times 100\%.$$

*polyethylene oxide sorbitan mono-oleate

The results obtained in the above test are compiled in Table II:

TABLE II

| | Cupriuretic Activity | |
| --- | --- | --- |
| Test Compound | Dosage mmol/kg p.o. | Percentage Change from Control |
| D,L-α-amino-2-imidazolepropionic acid, | 1.0 | +345 |
| D-α-amino-2-imidazolepropionic acid | 1.0 | +143 |
| L-α-amino-2-imidazolepropionic acid | 1.0 | +475 |
| L-α-amino-2-imidazolepropionic acid | 0.3 | +273 |
| Methyl D,L-α-amino-2-imidazolepropionate | 1.0 | +241 |
| Methyl D-α-amino-2-imidazolepropionate | 1.0 | +277 |
| Methyl L-α-amino-2-imidazolepropionate | 0.3 | +237 |
| Ethyl D,L-α-amino-2-imidazolepropionate | 0.3 | +115 |
| Ethyl D-α-amino-2-imidazolepropionate | 1.0 | +266 |
| Ethyl D-α-amino-2-imidazolepropionate | 0.3 | +131 |
| Ethyl L-α-amino-2-imidazolepropionate | 0.3 | +154 |
| Benzyl D,L-α-amino-2-imidazolepropionate | 0.3 | +130 |
| Benzyl D-α-amino-2-imidazole- | 1.0 | +185 |

TABLE II-continued

| Test Compound | Cupriuretic Activity Dosage mmol/kg p.o. | Percentage Change from Control |
|---|---|---|
| propionate | 0.3 | +56 |
| Benzyl L-α-amino-2-imidazole-propionate | 1.0 | +302 |
| | 0.3 | +176 |
| D,L-α-amino-α-methyl-2-imidazole-propionic acid | 1.0 | +55 |
| D,L-α-amino-4,5-dimethyl-2-imidazolepropionic acid | 1.0 | +12 |
| D,L-α-amino-2-imidazolepropionamide | 1.0 | +184 |
| D,L-α-amino-N—methyl-2-imidazole-propionamide | 1.0 | +168 |
| D,L-α-amino-N,N—dimethyl-2-imidazolepropionamide | 1.0 | +200 |

The D,L-compounds of formula I in which $R^1$, $R^2$ and $R^3$ each is hydrogen and $R^4$ is hydroxy or methoxy are known.

All of the other compounds of formula I as well as their pharmaceutically acceptable salts are provided by the present invention. The invention also provides a process for their preparation.

In a particular embodiment, the present invention relates to compounds of formula I, wherein $R^4$ is other than hydroxy or methoxy when $R^1$, $R^2$ and $R^3$ each is hydrogen.

Preferred compounds of formula I are those in which $R^1$, $R^2$ and $R^3$ each is hydrogen and $R^4$ is lower alkoxy containing at least 2 carbon atoms. An especially preferred compound of formula I is ethyl D-α-amino-2-imidazolepropionate.

The compounds of formula I and their pharmaceutically acceptable salts can be prepared as follows:

(a) for the preparation of a D,L-compound of formula I in which at least one of $R^1$, $R^2$ and $R^3$ is lower alkyl and $R^4$ is hydroxy, by debenzylating a D,L-compound of the formula

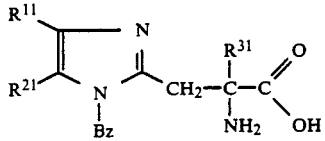

wherein $R^{11}$, $R^{21}$ and $R^{31}$ each individually is hydrogen or lower alkyl, with the proviso that at least one of $R^{11}$, $R^{21}$ and $R^{31}$ is lower alkyl, and Bz is benzyl.

(b) for the preparation of a D,L-, or L-compound of formula I in which $R^4$ is lower alkoxy containing at least 2 carbon atoms, or of a D- or L-compound of formula I in which $R^4$ is methoxy, or of a D,L-compound of formula I in which $R^4$ is aryl-(lower alkoxy), by esterifying a corresponding D,L-, D- or L-compound of formula I in which $R^4$ is hydroxy. or (c) for the preparation of a D,L-, D- or L-compound of formula I in which $R^4$ is amino, mono(lower alkyl)-amino or di(lower alkyl)amino, by amidating a corresponding D,L-, D- or L-compound of formula I in which $R^4$ is hydroxy or lower alkoxy, or (d) for the preparation of a D,L-, D- or L-compound of formula I in which $R^4$ is lower alkoxy containing at least 2 carbon atoms or aryl-(lower alkoxy), or of a D- or L-compound of formula I in which $R^4$ is methoxy, by hydrolyzing a D,L-, D- or L-compound of the formula

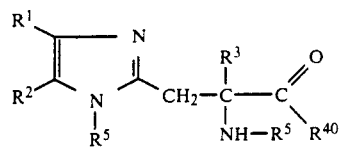

wherein $R^1$, $R^2$ and $R^3$ have the significance given earlier, $R^{40}$ is lower alkoxy or aryl-(lower alkoxy) and $R^5$ is tert.butoxycarbonyl, (e) for the preparation of a D- or L-compound of formula I in which $R^4$ is hydroxy, or of a D,L-compound of formula I in which at least one of $R^1$, $R^2$ and $R^3$ is lower alkyl and $R^4$ is hydroxy, by hydrolyzing a corresponding D-, L- or D,L-compound of formula I in which $R^4$ is lower alkoxy, or (f) for the preparation of a D- or L-compound of formula I, by resolving a D,L-compound of formula I and isolating the D- or L-compound, and, if desired, converting a compound of formula I obtained into a pharmaceutically acceptable salt.

The debenzylation of a compound of formula II in accordance with embodiment (a) of the foregoing process can be carried out in a generally known manner such as by treatment with sodium in liquid ammonia.

The esterification in accordance with embodiment (b) of the foregoing process can be carried out in a known manner. For example, the esterification can be carried out by reacting a compound of formula I in which $R^4$ is hydroxy with a lower alkanol, for example, methanol, ethanol and the like; or an aryl-substituted lower alkanol, for example, benzyl alcohol and the like in the presence of a strong acid such as, for example, a hydrohalic acid such as hydrochloric acid and the like, or a sulfonic acid, for example, p-toluenesulfonic acid and the like.

The amidation in accordance with embodiment (c) of the foregoing process can also be carried out in a known manner. Preferably, the amidation is carried out by reacting a compound of formula I in which $R^4$ is lower alkoxy with ammonia, a lower alkylamine, for example, methylamine and the like; or a di(lower alkyl)amine, for example, dimethylamine and the like, suitably in an inert organic solvent, for example, a lower alkanol such as methanol and the like.

The hydrolysis of a compound of formula III in accordance with embodiment (d) of the process can be carried out in a known manner using hydrogen chloride in dioxan.

The hydrolysis in accordance with embodiment (e) of the foregoing process can also be carried out in a known manner using hydrochloric acid.

The resolution of a racemic mixture of formula I into its respective enantiomers, that is its D- and L-enantiomers in accordance with embodiment (f) of the foregoing process can be carried out in a known manner. For example, the resolution can be carried out by treating a racemic mixture of formula I with an optically active acid such as D-tartaric acid, L-tartaric acid, dibenzoyl-D-tartaric acid, dibenzoyl-L-tartaric acid and the like, separating the two diastereoisomeric salts obtained, for example, by fractional crystallization and liberating the optically uniform enantiomers from these salts.

The conversion of a thus-obtained compound of formula I into a pharmaceutically acceptable salt can be carried out by treatment with a pharmaceutically acceptable acid or a pharmaceutically acceptable base according to generally known methods.

Compounds of formula II which, as indicated above, are starting materials in the preparation of compounds of formula I are either known compounds or analogues of known compounds which can be prepared in an analogous manner to the known compound.

The invention also provides compounds of formula IIIa which, as indicated above, are starting materials in the preparation of compounds of formula I. They can be prepared by reacting a D,L-, D- or L-compound of formula I in which $R^4$ is hydroxy with di-tert.butyl dicarbonate and esterifying the resulting D,L-, D- or L-compound of the formula

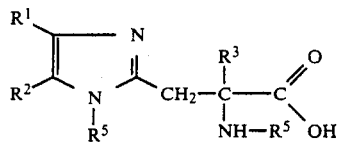

IIIb wherein $R^1$, $R^2$, $R^3$ and $R^5$ are as described above.

The reaction of a compound of formula I in which $R^4$ is hydroxy with di-tert.butyl dicarbonate can be carried out in a conventional manner in the presence of a base, for example, an alkali metal hydroxide such as sodium hydroxide or potassium hydroxide) and in an inert organic solvent, for example, a cyclic ether such as dioxane, suitably at about 0° C.

The esterification of a compound of formula IIIb can also be carried out in a conventional manner using an appropriate diazoalkane, for example, diazomethane and the like; or an appropriate aryl-diazoalkane, for example, phenyldiazomethane and the like; conveniently in an inert organic solvent, for example, an ether like diethyl ether and the like; and at about room temperature.

The invention provides compounds of formula IIIb.

The invention provides: pharmaceutical preparations containing a compound of formula I; a process for the preparation of such pharmaceutical preparations; the compounds of formula I with the exception of the D,L-compounds of formula I in which $R^1$, $R^2$ and $R^3$ each represent hydrogen and $R^4$ represents hydroxy or methoxy, which are known; a process for the preparation of the compounds; the use of the compounds of formula I and the preparations containing the same in the treatment of degenerative joint diseases and of Wilson's disease; and intermediates in the preparation of the compounds of formula I.

The following Examples illustrate the present invention:

I. PHARMACEUTICAL PREPARATIONS

Example 1

Tablets containing the following ingredients are manufactured in a conventional manner:

| | |
|---|---|
| Ethyl D-α-amino-2-imidazolepropionate | 400 mg |
| Microcrystalline cellulose | 70 mg |
| Calcium phosphate dihydrate | 136 mg |
| Sodium starch glycolate | 30 mg |
| Polyvinylpyrrolidone | 20 mg |
| Talc | 30 mg |
| Magnesium stearate | 4 mg |
| Total weight | 690 mg |

Example 2

Hard gelatine capsules containing the following ingredients are manufactured in a conventional manner:

| | |
|---|---|
| Ethyl D-α-amino-2-imidazolepropionate | 200 mg |
| Mannitol | 150 mg |
| Starch | 72 mg |
| Sodium dioctylsulphosuccinate | 1 mg |
| Talc | 15 mg |
| Magnesium sulphate | 2 mg |
| Capsule fill weight | 440 mg |

Example 3

A syrup containing the following ingredients is manufactured in a conventional manner:

| | |
|---|---|
| Ethyl D-α-amino-2-imidazolepropionate | 200 mg |
| Sorbitol (70% aqueous solution) | 2 mg |
| Citric acid | 1.5 mg |
| Saccharin | 10 mg |
| Flavour | 10 mg |
| Colour | 1 mg |
| Methyl p-hydroxybenzoate | 5 mg |
| Propyl p-hydroxybenzoate | 1 mg |
| Distilled water ad | 5 ml |

Example 4

A solid preparation containing the following ingredients is manufactured in a conventional manner:

| | |
|---|---|
| Ethyl D-α-amino-2-imidazolepropionate | 200 mg |
| Sucrose | 1.8 mg |
| Citric acid | 2 mg |
| Sodium cyclamate | 10 mg |
| Sodium saccharin | 5 mg |
| Colour | 1 mg |
| Flavour | 4 mg |
| Hydroxypropylmethylcellulose | 5 mg |

This solid preparation is reconstituted with sufficient water to provide 5 ml of a palatable syrup at the time of use.

Example 5

Tablets containing the following ingredients are manufactured in a conventional manner:

| | |
|---|---|
| D,L-α-amino-2-imidazolepropionic acid | 250 mg |
| Microcrystalline cellulose | 130 mg |
| Calcium phosphate dihydrate | 170 mg |
| Sodium starch glycolate | 30 mg |
| Talc | 37 mg |
| Magnesium stearate | 3 mg |
| Total weight | 620 mg |

Example 6

Tablets containing the following ingredients are manufactured in a conventional manner:

| | |
|---|---|
| D,L-α-amino-2-imidazolepropionic acid | 125 mg |

| | |
|---|---|
| Mannitol | 70 mg |
| Microcrystalline cellulose | 70 mg |
| Sodium starch glycolate | 20 mg |
| Hydroxypropylmethylcellulose | 8 mg |
| Talc | 15 mg |
| Magnesium stearate | 2 mg |
| Total weight | 310 mg |

Example 7

Hard gelatine capsules containing the following ingredients are manufactured in a conventional manner:

| | |
|---|---|
| D.L-α-amino-2-imidazolepropionic acid | 200 mg |
| Mannitol | 150 mg |
| Starch | 72 mg |
| Sodium dioctylsulphosuccinate | 1 mg |
| Talc | 15 mg |
| Magnesium stearate | 2 mg |
| Total capsule | 440 mg |

Example 8

A syrup containing the following ingredients is manufactured in a conventional manner:

| | |
|---|---|
| D,L-α-amino-2-imidazolepropionic acid | 200 mg |
| Sorbitol (70% aqueous solution) | 2 g |
| Citric acid | 1.5 mg |
| Saccharin | 10 mg |
| Flavour | 10 mg |
| Colour | 1 mg |
| Methyl p-hydroxybenzoate | 5 mg |
| Propyl p-hydroxybenzoate | 1 mg |
| Distilled water ad | 5 ml |

Example 9

A solid preparation containing the following ingredients is manufactured in a conventional manner:

| | |
|---|---|
| D,L-α-amino-2-imidazolepropionic acid | 200 mg |
| Sucrose | 1.8 g |
| Citric acid | 2 mg |
| Sodium cyclamate | 10 mg |
| Sodium saccharin | 5 mg |
| Colour | 1 mg |
| Flavour | 4 mg |
| Hydroxypropylmethylcellulose | 5 mg |

This solid preparation is reconstituted with sufficient water to provide 5 ml of a palatable syrup at the time of use.

II. PREPARATION OF NOVEL COMPOUNDS OF FORMULA I AND THEIR PHARMACEUTICALLY ACCEPTABLE SALTS

Example 10

3.1 g of L-α-amino-2-imidazolepropionic acid were suspended in 60 ml of methanol and dry hydrogen chloride was passed into the suspension while stirring and cooling with ice. A clear solution was soon obtained and the passage of gas was continued until the solution was saturated (1.25 hours). The resulting solution was left to stand at room temperature overnight and then evaporated to dryness. The residue was dissolved in 10 ml of methanol and the solution was diluted with 100 ml of dry diethyl ether. A syrup precipitated and, on seeding, gave a white solid which was filtered off, washed with diethyl ether and dried. There were obtained 4.79 g of product of melting point 189° C. (effervescence), $[\alpha]_D^{20} = +43.4°$ (c=0.99% in 0.1N hydrochloric acid). This material was dissolved in 50 ml of methanol/ethyl acetate (1:1) by boiling, the solution was filtered while hot and ethyl acetate was added to the boiling filtrate until crystallization commenced, 15 ml of ethyl acetate being required. The mixture was left to cool to room temperature and was then stored in a refrigerator overnight, there being obtained 3.3 g of methyl L-α-amino-2-imidazolepropionate dihydrochloride of melting point 189° C. (effervescence), $[\alpha]_D^{20} = +43.7°$ (c=1.05% in 0.1N hydrochloric acid).

Analysis for $C_7H_{11}N_3O_2.2HCl$: Calculated C: 34.7; H: 5.4; N: 17.4; Cl: 29.3%. Found: C: 34.6; H: 5.4; N: 17.5; Cl: 29.5%.

Example 11

In a manner analogous to that described in Example 10, from 3.1 g of D-α-amino-2-imidazolepropionic acid there were obtained 3.1 g of methyl D-α-amino-2-imidazolepropionate dihydrochloride of melting point 189° C. (effervescence), $[\alpha]_D^{20} = -43.3°$ (c=0.97% in 0.1N hydrochloric acid).

Analysis for $C_7H_{11}N_3O_2.2HCl$: Calculated: C: 34.7; H: 5.4; N: 17.4; Cl: 29.3%. Found: C: 34.6; H: 5.4; N: 17.4; Cl: 29.4%.

Example 12

A suspension of 5 g (32 mmol) of D,L-α-amino-2-imidazolepropionic acid in 100 ml of ethanol was stirred and cooled in ice while dry hydrogen chloride gas was passed into the mixture until it was saturated. The mixture was stirred at room temperature for 75 hours. The resulting clear solution was evaporated to dryness, the residue was dissolved in 5 ml of water and the solution was diluted with 100 ml of acetonitrile. A syrup precipitated and crystallized slowly to give a white solid. This solid was filtered off, washed with acetonitrile and dried in the air at room temperature overnight. There were obtained 9.8 g of product of melting point 45°–48° C. After recrystallization from 5 ml of water, there were obtained 3.0 g of ethyl D,L-α-amino-2-imidazolepropionate dihydrochloride trihydrate in the form of colourless crystals of melting point 46°–48.5° C.

Analysis for $C_8H_{13}N_3O_2.2HCl.3H_2O$ Calculated: C: 31.0; H: 6.8; N: 13.6; $H_2O$: 17.4%. Found: C: 31.0; H: 6.6; N: 13.6; $H_2O$: 17.2%.

Example 13

In a manner analogous to that described in Example 12, from 2.0 g (13 mmol) of D-α-amino-2-amidazolepropionic acid there were obtained, after recrystallization from water, 1.4 g of ethyl D-α-amino-2-imidazolepropionate dihydrochloride trihydrate of melting point 59°–61° C. $[\alpha]_D^{20} = -40.3°$ (c=1.00% in water).

Analysis for $C_8H_{13}N_3O_2.2HCl.3H_2O$: Calculated: C: 31.0; H: 6.8; N: 13.6; $H_2O$: 17.4%. Found: C: 30.7; H: 6.6; N: 13.6; $H_2O$: 18.0%.

Example 14

In a manner analogous to that described in Example 12, from 2.0 g (13 mmol) of L-α-amino-2-imidazolepropionic acid there was obtained, after recrystallization from water, 1.0 g of ethyl L-α-amino-2-imidazolepropionate dihydrochloride trihydrate of melting point 59°–61° C., $[α]_D^{20} = +40.3°$ (c = 1.01% in water).

Analysis for $C_8H_{13}N_3O_2.2HCl.3H_2O$. Calculated: C: 31.0; H: 6.8; N: 13.6; $H_2O$: 17.4%. Found: C: 31.0; H: 6.6; N: 13.7; $H_2O$: 17.6%.

Example 15

68 g (0.22 mol) of ethyl D,L-α-amino-2-imidazolepropionate dihydrochloride trihydrate were suspended in 680 ml of ethanol and the suspension was stirred while a solution of 10.1 g (0.44 g atom) of sodium in 200 ml of ethanol was added. The mixture was stirred for 30 minutes and then evaporated to dryness. The residue was triturated with 1 l of chloroform and filtered through Hyflo in order to remove sodium chloride. Evaporation of the filtrate gave 41.2 g of crystalline ethyl D,L-amino-2-imidazolepropionate. This material was dissolved in 590 ml of ethanol and a solution of 84.7 g (0.22 mol) of (+)-dibenzoyl-D-tartaric acid monohydrate in 590 ml of ethanol was added. The solution was left to stand in a refrigerator for 20 hours. The mass of hard crystals which formed was broken up and the mixture was left to stand in a refrigerator for a further 24 hours. The product was filtered off, washed with two 50 ml portions of ethanol and then dried to constant weight to give 60.1 g of crude dibenzoyl-D-tartrate salt of melting point 140°–141.5° C. (decomposition), $[α]_D^{20} = +69.8°$ (c = 0.99% in methanol). Recrystallization of this product from 1.1 l of ethanol containing 20 ml of water gave 44.6 g of material of melting point 143°–145° C. (decomposition), $[α]_D^{20} = +67.6°$ (c = 1.00% in methanol). A final recrystallization from 1.5 l of ethanol containing 4 ml of water gave 32.8 g of ethyl D-α-amino-2-imidazolepropionate dibenzoyl-D-tartrate of melting point 141°–145° C. (decomposition), $[α]_D^{20} = +65.9°$ (c = 1.00% in methanol).

Analysis for $C_{26}H_{27}N_3O_{10}.1.1H_2O$: Calculated: C: 55.6; H: 5.2; N: 7.5; $H_2O$: 3.5%. Found: C: 55.4; H: 5.2; N: 7.4; $H_2O$: 3.6%.

31.8 g (0.057 mol) of ethyl D-α-amino-2-imidazolepropionate dibenzoyl-D-tartrate were suspended in 400 ml of ethanol. A solution of hydrogen chloride in ethanol (32 mol of approximately 5.6M) was introduced while stirring to give a clear solution which was evaporated to dryness. The residual syrup was shaken with 18 ml of water until a homogeneous mixture was obtained. This mixture was treated with 360 ml of acetonitrile and cooled. The crystals which separated were filtered off, washed with acetonitrile and dried in the air overnight. There were obtained 16.4 g of product of melting point 58.5°–61° C. Recrystallization from 8 ml of water gave 8.3 g of ethyl D-α-amino-2-imidazolepropionate dihydrochloride trihydrate of melting point 59°–61° C., $[α]_D^{20} = -41.4°$ (c = 0.99% in water).

Analysis for $C_8H_{13}N_3O_2.2HCl.3H_2O$: Calculated: C: 31.0; H: 6.8; N: 13.55; $H_2O$: 17.4%. Found: C: 31.1; H: 6.8; N: 13.5; $H_2O$: 17.3%.

The mother liquors obtained after filtration of the initial crop of ethyl D-α-amino-2-imidazolepropionate dibenzoyl-D-tartrate deposited a second crop of solid on standing. This was filtered off and dried, there being obtained 11.2 g of melting point 140°–142° C. (decomposition), $[α]_D^{20} = +77.1°$ (c = 1.01% in methanol). The filtrate was treated with a solution of hydrogen chloride in ethanol (100 ml of approximately 4M) and evaporated to dryness. The residue was shaken with 31 ml of water until a homogeneous mixture was obtained. This mixture was treated with 620 ml of acetonitrile and the resulting mixture was stored in a refrigerator. The crystalline solid which formed was filtered off, washed with acetonitrile and dried in the air for 24 hours. There were obtained 24.2 g of product of melting point 59°–61° C. Recrystallization from 16 ml of water gave 9.0 g of ethyl L-α-amino-2-imidazolepropionate dihydrochloride trihydrate of melting point 58.5°–60.5° C. $[α]_D^{20} = +41.2$ (c = 1.05% in water).

Analysis for $C_8H_{13}N_3O_2.2HCl.3H_2O$: Calculated: C: 31.0; H: 6.8; N: 13.55; $H_2O$: 17.4%. Found: C: 31.1; H: 6.65; N: 13.6; $H_2O$: 17.4%.

Example 16

40 g (0.22 mol) of ethyl D,L-α-amino-2-imidazolepropionate were resolved according to the procedure described in Example 15 using 82.2 g (0.22 mol) of (−)-dibenzoyl-L-tartaric acid as the resolving agent. The crude salt (49.8 g) was recrystallized once from 1 l of ethanol containing 3 ml of water to give 39.5 g of ethyl L-α-amino-2-imidazolepropionate dibenzoyl-L-tartrate of melting point 145.5°–148° C., $[α]_D^{20} = -65.4°$ (c = 1.00% in methanol).

The foregoing ethyl L-α-amino-2-imidazolepropionate dibenzoyl-L-tartrate was converted into ethyl L-α-amino-2-imidazolepropionate dihydrochloride trihydrate in a manner analogous to that described in Example 15, there being obtained, after recrystallization from water, 10.8 g of melting point 58.5°–60.5° C. $[α]_D^{20} = +41.0°$ (c = 1.01% in water).

Analysis for $C_8H_{13}N_3O_2.2HCl.3H_2O$: Calculated: C: 31.0; H: 6.8; N: 13.55; $H_2O$: 17.4%. Found: C: 31.15; H: 6.8; N: 13.7; $H_2O$: 17.7%.

Optically pure ethyl D-α-amino-2-imidazolepropionate could not be obtained directly from the mother liquors of the foregoing resolution. It was therefore found necessary to convert the D-enriched ester dihydrochloride into the free base and to treat this with (+)-dibenzoyl-D-tartaric acid. The resulting dibenzoyl-D-tartrate salt was crystallized to constant rotation from ethanol/water and converted into the dihydrochloride as described in Example 15. Recrystallization from water gave 8.3 g of pure ethyl D-α-amino-2-imidazolepropionate dihydrochloride trihydrate of melting point 59°–61° C., $[α]_D^{20} = -41.4°$ (c = 0.99% in water).

Analysis for $C_8H_{13}N_3O_2.2HCl.3H_2O$: Calculated: C: 31.0; H: 6.8; N: 13.55; $H_2O$: 17.4%. Found: C: 31.1; H: 6.8; N: 13.5; $H_2O$: 17.3%.

Example 17

34.5 g (0.19 mol) of ethyl D-α-amino-2-imidazolepropionate were dissolved in 350 ml of ethanol and 185 ml of a standard solution of 1N hydrochloric acid were added. The solution was evaporated to dryness and the residue was co-evaporated with ethanol in order to remove water. The crude monohydrochloride was dissolved in 140 ml of 95% ethanol and the solution was diluted with 140 ml of ethyl acetate. The mixture was heated to boiling and filtered. The filtrate was left to cool, finally in a refrigerator overnight. The crystalline solid was filtered off, washed with ethyl acetate and dried in the air for 24 hours to give 32.7 g of ethyl D-α-amino-2-imidazolepropionate monohydrochloride hemihydrate of melting point 98.5°–100.5° C., $[α]_D^{20} = -54.8°$ (c = 1.00% in 1N hydrochloric acid).

Analysis for $C_8H_{13}N_3O_2.HCl.0.5H_2O$: Calculated: C: 42.0; H: 6.6; N: 18.4; Cl 15.5; $H_2O$: 3.9%. Found: C: 41.8; H: 6.6; N: 18.5; Cl 15.45; $H_2O$: 4.5%.

EXAMPLE 18

A solution of 10 g of ethyl D-α-amino-2-imidazolepropionate dihydrochloride trihydrate in 100 ml of 6N hydrochloric acid was boiled under reflux for 2 hours. The mixture was evaporated to dryness under reduced pressure at 40° C. The residue was then evaporated twice with 40 ml of water each time in order to remove most of the hydrochloric acid. The residue was thereupon dissolved in 50 ml of water and the solution was passed through a column containing 150 g of Zerolit 225 cation exchange resin (H+ form). The column was washed thoroughly with water until the eluate was neutral. The D-α-amino-2-imidazolepropionic acid was then eluted using 1N ammonia. Fractions were collected and those showing a ninhydrin positive spot were combined and evaporated to dryness to give 4.7 g of a white solid. For recrystallization, this solid was dissolved in 40 ml of water, the solution was heated to 70° C. and 40 ml of ethanol were added. The solution was filtered while hot, seeded and left to crystallize in a refrigerator to give 3.8 g of D-α-amino-2-imidazolepropionic acid of melting point 240° C. (decomposition), $[α]_D^{20} = +27.6°$ (c=1.08% in water).

Analysis for $C_6H_9N_3O_2$: Calculated: C: 46.45; H: 5.85; N: 27.1%. Found: C: 46.7; H: 5.8; N: 27.2%.

EXAMPLE 19

Ethyl L-α-amino-2-imidazolepropionate dihydrochloride trihydrate was hydrolyzed in a manner analogous to that described in Example 18 to give L-α-amino-2-imidazolepropionic acid of melting point 239° C. (decomposition), $[α]_D^{20} = -27.6°$ (c=1.00% in water).

Analysis for $C_6H_9N_3O_2$: Calculated: C: 46.45; H: 5.85; N: 27.1%. Found: C: 46.2; H: 5.7; N: 27.0%.

EXAMPLE 20

A mixture of 1.48 g (9.55 mmol) of D,L-α-amino-2-imidazolepropionic acid, 3.8 g (20 mmol) of p-toluenesulphonic acid monohydrate, 10 ml of benzyl alcohol and 10 ml of chloroform was stirred and the mixture was heated under reflux briskly in an apparatus fitted with a soxhlet extractor. The soxhlet was charged with a thimble containing 12 g of 4 A molecular sieves and filled with 22 ml of chloroform. The mixture was heated under reflux for 30 hours, the molecular sieves being renewed after 18 hours. The mixture was then evaporated to a low bulk under reduced pressure and the residual yellow gum was triturated with two 30 ml portions of diethyl ether in order to remove unreacted benzyl alcohol. The gum was dissolved in 30 ml of chloroform and the solution was shaken with 4 ml of saturated potassium carbonate solution and 10 ml of water. Three layers separated on standing. The lower and middle layers were run off and shaken with 20 ml of water. After standing, only two layers formed. The lower chloroform layer was separated and filtered, whereafter the filtrate was dried over anhydrous sodium sulphate and evaporated under reduced pressure to give 2.0 g of a yellow oil. This oil was dissolved in 30 ml of dry tetrahydrofuran, the solution was cooled in an ice/salt mixture and hydrogen chloride gas was bubbled through the solution until no further precipitation occurred and the mixture was strongly acidic. The mixture was evaporated to dryness under reduced pressure, the residue was treated with two 20 ml portions of dry tetrahydrofuran and the mixture was evaporated under reduced pressure. The yellow solid obtained was suspended in 20 ml of acetonitrile, filtered off, washed with two 10 ml portions of acetonitrile and dried in vacuo, there being obtained 1.0 g of product. Recrystallization from water gave 0.5 g of benzyl D,L-α-amino-2-imidazolepropionate dihydrochloride in the form of white crystals of melting point 190°-192° C.

Analysis for $C_{13}H_{15}N_3O_2.2HCl$: Calculated: C: 49.1; H: 5.4; N: 13.2%. Found: C: 49.1; H: 5.4; N: 13.4%.

EXAMPLE 21

53 g of D,L-α-amino-α-methyl-1-benzyl-2-imidazolepropionic acid dihydrochloride were placed in a 2.5 l four-necked round-bottomed flask, fitted with an air stirrer and ammonia condenser, stirred slowly and cooled in an acetone/dry-ice bath while 1 l of ammonia was condensed into the flask. Small pieces of freshly cut sodium (about 24 g) were then added until a permanent deep blue colour persisted for about 20 minutes. Ammonium chloride was then added in order to destroy the blue colour. The ammonia was allowed to evaporate overnight. About 60 ml of water were added to the residue, the mixture was evaporated in order to remove the toluene produced during the reaction, the residue was again dissolved in water and the solution was adjusted to pH 8.5 by means of concentrated hydrochloric acid. After evaporation to dryness in vacuo, the residue was dissolved in a minimum volume of hot water and left to crystallize. There were obtained 13.6 g of product of melting point 158°-165° C. After crystallization from water, there were obtained 4.8 g of product of melting point 160°-170° C. This product was dissolved in water and concentrated hydrochloric acid was added to pH 3. After evaporation to dryness in vacuo and evaporation with toluene, the solid obtained was taken up in ethanol and, on standing, the product precipitated and was subsequently filtered off. There were obtained 3.8 g of D,L-α-amino-α-methyl-2-imidazolepropionic acid hydrochloride of melting point 264°-267° C.

Analysis for $C_7H_{11}N_3O_2.HCL$: Calculated: C: 40.9; H: 5.9; N: 20.4%. Found: C: 40.8; H: 6.0; N: 20.2%.

The D,L-α-amino-α-methyl-1-benzyl-2-imidazolepropionic acid dihydrochloride used as the starting material was prepared as follows:

14.5 g (483 mmol) of sodium hydride (80% in oil) were washed with petroleum ether (40°-60° C.) and the petroleum ether was decanted off. The washed sodium hydride was suspended in 200 ml of dry dimethylformamide, the suspension was cooled in an ice-bath and 55 g (433 mmol) of ethyl 2-isocyanopropionate in 100 ml of dry dimethylformamide were added dropwise. After completion of the addition, the mixture was allowed to warm to room temperature and was then stirred at this temperature for 1 hour. 53 g (218 mmol) of 1-benzyl-2-chloromethylimidazole hydrochloride were then added portionwise and the mixture was left to stir at room temperature overnight. The mixture was poured into 1.5 l of water while stirring and the aqueous mixture was extracted with five 200 ml portions of ethyl acetate. The combined ethyl acetate extracts were washed with saturated sodium chloride solution and water, dried over anhydrous potassium carbonate and evaporated to give a yellow oil which crystallized after standing overnight. The crystals were filtered off in a fume cupboard and washed with 5% ethyl acetate/hexane. There were thus obtained 47 g of ethyl D,L-α-isocyano-α-methyl-1-benzyl-2-imidazolepropionate of melting point 66°-68° C.

47 g of ethyl D,L-α-isocyano-α-methyl-1-benzyl-2-imidazolepropionate were added portionwise to 500 ml of concentrated hydrochloric acid while stirring. After completion of the addition, the mixture was heated at 100° C. for 3 hours, then cooled to room temperature and evaporated to dryness, there being obtained a brown oil. After repeated evaporation with toluene, the oil gave 53 g of D,L-α-amino-α-methyl-1-benzyl-2-imidazolepropionic acid dihydrochloride in the form of a very hygroscopic brown foam which must be stored in a closed container. If desired, the foam can be recrystallized from isopropyl alcohol and then melts at 225°–228° C.

Analysis for $C_{14}H_{17}N_3O_2 \cdot 2HCl$ Calculated: C: 50.6; H: 5.8; N: 12.65%. Found: C: 50.8; H: 5.6; N: 12.6%.

EXAMPLE 22

A suspension of 11 g (40 mmol) of D,L-α-amino-1-benzyl-4,5-dimethyl-2-imidazolepropionic acid in 80–100 ml of liquid ammonia was stirred and cooled in an acetone/dry-ice bath. Sodium metal was added portionwise over a period of 1 hour until a blue colour persisted for 20 minutes, 1.5 g of sodium being required. The ammonia was allowed to evaporate, the residue was taken up in 30 ml of water and then neutralized to pH 7 by the addition of glacial acetic acid. A crystalline solid separated. This solid was filtered off, washed with water, ethanol and diethyl ether and then dried to give 2.4 g of product of melting point 213°–214° C. (decomposition). Recrystallization from water yielded D,L-α-amino-4,5-dimethyl-2-imidazolepropionic acid of melting point 217°–218° C. (decomposition). After drying for 4 hours at 90° C./0.1 mm, the melting point was 169°–170° C.

Analysis for $C_8H_{13}N_3O_2 \cdot 0.2H_2O$: Calculated C: 51.4; H: 7.2; N: 22.5; $H_2O$: 1.9%. Found: C: 51.4; H: 7.2; N: 22.5; $H_2O$: 2.25%.

The D,L-α-amino-1-benzyl-4,5-dimethyl-2-imidazolepropionic acid used as the starting material was prepared as follows:

A mixture of 8 g (43 mmol) of 1-benzyl-4,5-dimethylimidazole and 60 ml of 40% aqueous formaldehyde solution was heated in a sealed autoclave at 150° C. for 20 hours. The mixture was evaporated and the semi-solid residue was chromatographed on a column of 300 g of silica gel using a 20% solution of methanol in chloroform for the elution. Evaporation of the eluate yielded 6 g of 1-benzyl-4,5-dimethyl-2-hydroxymethylimidazole of melting point 156°–158° C. After recrystallization from methylcyclohexane, the melting point was 160°–162° C. A portion of the product was treated with a solution of hydrogen chloride in ethanol. Addition of diethyl ether precipitated 1-benzyl-4,5-dimethyl-2-hydroxymethylimidazole hydrochloride of melting point 162°–163° C.

Analysis for $C_{13}H_{16}N_2O \cdot HCl$: Calculated: C: 61.8; H: 6.8; N: 11.1%. Found: C: 61.6; H: 6.7; N: 11.15%.

A suspension of 15 g (69 mmol) of 1-benzyl-4,5-dimethyl-2-hydroxymethylimidazole in 50 ml of dichloromethane was added portionwise over a period of 30 minutes to a stirred solution of 25 ml of thionyl chloride in 25 ml of dichloromethane. The solution obtained was boiled under reflux for 1.5 hours and then left to stand at room temperature overnight. Evaporation of the solution gave 23.5 g of crude 1-benzyl-2-chloromethyl-4,5-dimethylimidazole hydrochloride in the form of an oil which was used in the next step without further purification.

40 g (184 mmol) of diethyl acetamidomalonate were added to a solution of 6.3 g (0.27 g atom) of sodium in 250 ml of ethanol. The solution was stirred for 20 minutes, then cooled in ice and treated with a solution of 23.5 g of crude 1-benzyl-2-chloromethyl-4,5-dimethylimidazole hydrochloride in 40 ml of ethanol. The mixture was stirred at room temperature overnight and evaporated. The residue was taken up in 300 ml of 2N hydrochloric acid, the solution was filtered and the filtrate was shaken with 100 ml portions of ethyl acetate until diethyl acetamidomalonate was no longer extracted. The aqueous solution was treated with an excess of solid sodium carbonate. An oil separated and was extracted into ethyl acetate. The ethyl acetate solution was dried over magnesium sulphate and evaporated to give 15.4 g of crude diethyl 1-benzyl-4,5-dimethyl-2-imidazolylmethylacetamidomalonate in the form of an oil which subsequently crystallized. This material was used in the next step without further purification.

A solution of 34 g of crude diethyl 1-benzyl-4,5-dimethyl-2-imidazolylmethylacetamidomalonate in 170 ml of concentrated hydrochloric acid was heated under reflux at 130° C. for 15 hours. The mixture was evaporated, the residue was treated with water and evaporated again. The residue was taken up in 100 ml of water and the solution was neutralized to pH 7.2 by the addition of 2N sodium hydroxide solution. After storing in a refrigerator overnight, the precipitated solid was filtered off, washed with water, acetone and diethyl ether and then dried. There were obtained 11.5 g of product of melting point 224°–225° C. (decomposition) which was purified by dissolution in dilute ammonia solution followed by neutralization to pH 7.5 using dilute acetic acid. There was thus obtained D,L-α-amino-1-benzyl-4,5-dimethyl-2-imidazolepropionic acid of melting point 224°–225° C. (decomposition).

Analysis for $C_{15}H_{19}N_3O_2$: Calculated C: 65.9; H: 7.0; N: 15.4%. Found: C: 65.7; H: 6.9; N: 15.4%.

EXAMPLE 23

A suspension of 5 g of methyl D,L-α-amino-2-imidazolepropionate in 50 ml of dry methanol was protected from moisture, stirred and cooled in an ice/salt mixture. Dimethylamine gas was bubbled through the stirred suspension at such a rate that a clear solution had formed after about 15 minutes and the solution was almost saturated after 30 minutes. The flow of gas was then discontinued, the solution was stirred for a further 2 hours while allowing to warm slowly to room temperature and then left to stand at room temperature overnight. If any unreacted methyl ester was present at this stage (as determined by evaporating an aliquot of the solution to dryness and examining the residue by nuclear magnetic resonance spectroscopy), the passage of dimethylamine while cooling in ice/salt and overnight storage at room temperature was repeated. The solution was evaporated to dryness at 40° C. under reduced pressure and the residue was dissolved in 40 ml of water. A small amount of insoluble material was removed by filtration, the filtrate was passed through a column of 50 ml of Dowex 1-X8 ion-exchange resin ($OH^-$ form) and the column was eluted with water until the pH of the eluate was less than 8. The total volume eluted was 250 ml. The eluate was evaporated at 40° C. under reduced pressure to give a pale yellow oil which crystallized on standing. This material was dissolved in 20 ml of warm ethanol, a solution of hydrogen chloride in ethanol (10 ml; 5.7N) was added and the strongly acidic solution was stored in a refrigerator overnight, during which time the product crystallized. The white solid was filtered off, washed with ethanol and diethyl ether and dried at 50° C. in vacuo over phosphorus pentoxide, there being obtained 5 g of product of melting point 223°–224° C. (decomposition). For purification, this product was dissolved in 5 ml of warm water, 20 ml of ethanol were added, the solution was filtered, the filtrate was diluted with 80 ml of ethanol and the solution was left to stand at room temperature for 4 hours to crystallize. The mixture was then stored in a refrigerator overnight. The white crystalline product was filtered off, washed with ethanol and diethyl ether and then dried at 50° C. in vacuo over phosphorus pentoxide, there being obtained 4.0 g of D,L-α-amino-N,N-dimethyl-2-imidazolepropionamide dihydrochloride of melting point 231°–232° C. (decomposition).

Analysis for $C_8H_{14}N_4O.2HCl$: Calculated: C: 37.7; H: 6.3; Cl: 27.8; N: 22.0%. Found: C: 37.5; H: 6.25; Cl: 27.9; N: 22.0%.

Example 24

In a manner analogous to that described in Example 23, from 5 g of methyl D,L-α-amino-2-imidazolepropionate and methylamine gas there was obtained 3.65 g of pure D,L-α-amino-N-methyl-2-imidazolepropionamide dihydrochloride in the form of white hydrated crystals of melting point 191°–193° C.

Analysis for $C_7H_{12}N_4O.2HCl.0.6H_2O$: Calculated: C: 33.4; H: 6.1; Cl: 28.1; N: 22.2%. Found: C: 33.3; H: 6.1; Cl: 27.9; N: 22.4%.

Example 25

In a manner analogous to that described in Example 23, from 5 g of methyl D,L-α-amino-2-imidazolepropionate and dry ammonia gas there were obtained 4 g of pure D,L-α-amino-2-imidazolepropionamide dihydrochloride in the form of white crystals of melting point 215°–217°C. (decomposition).

Analysis for $C_6H_{10}N_4O.2HCl$: Calculated: C: 31.7; H: 5.3; Cl: 31.2; N: 24.7%. Found: C: 31.7; H: 5.3; Cl: 31.3; N: 24.8%.

Example 26

(A) 10 g of benzyl D-α-tert.butoxycarbonylamino-1-tert.butoxycarbonyl-2-imidazolepropionate were dissolved in 400 ml of a 4N solution of hydrogen chloride in dioxan and the yellow solution obtained was stirred at room temperature for 2 hours. The solution was concentrated at 30° C. under reduced pressure to about three quarters of its original volume, whereupon a gum separated. 500 ml of anhydrous diethyl ether were added and the mixture was left to stand in a refrigerator for 2 hours. The yellow supernatant liquor was decanted off. The gum was treated with a further 250 ml of diethyl ether, whereupon it solidified. The solid was filtered off, washed with two 30 ml portions of diethyl ether and dried. Working-up of the mother liquors gave a further two crops of product. The total yield of deliquescent benzyl D-α-amino-2-imidazolepropionate dihydrochloride was 4.75 g.

The foregoing dihydrochloride was converted into the monohydrochloride as follows:

2.4 g (7.55 mmol) of the dihydrochloride were shaken with 15 ml of saturated potassium carbonate solution, 10 ml of water and 25 ml of chloroform, the layers were separated and the aqueous layer was extracted with three 10 ml portions of chloroform. The combined organic extracts were dried and evaporated to dryness under reduced pressure to give 2 g of crude benzyl D-α-amino-2-imidazolepropionate in the form of a brown oil. 1.84 g of this oil were dissolved in 50 ml of isopropanol and added to a solution of 2.2 g (6.92 mol) of benzyl D-α-amino-2-imidazolepropionate dihydrochloride in 50 ml of isopropanol. The solution was then filtered. The filtrate was seeded, evaporated to about half volume at room temperature under reduced pressure and then stored overnight at −20° C. The white crystalline monohydrochloride was filtered off, washed with 10 ml of cold isopropanol and with 20 ml of diethyl ether and dried. There were obtained 2.80 g (72%) of benzyl D-α-amino-2-imidazolepropionate monohydrochloride of melting point 114°–117° C., $[\alpha]_D^{20} = -18.5°$ (c = 1.0004% in 1N hydrochloric acid).

Analysis for $C_{13}H_{15}N_3O_2.HCl$: Calculated C: 55.4; H: 5.7; Cl: 12.6; N: 14.9%. Found: C: 55.3; H: 5.8; Cl: 12.7; N: 14.7%.

The benzyl D-α-tert.butoxycarbonylamino-1-tert.butoxycarbonyl-2-imidazolepropionate used as the starting material was prepared as follows:

(B) A mixture of 4.65 g (30 mmol) of D-α-amino-2-imidazolepropionic acid, 60 ml of 1N sodium hydroxide and 60 ml of dioxan was stirred, the resulting solution was cooled in an ice-bath and 16.35 g (75 mmol) of di-tert.butyl dicarbonate were added portionwise over a period of 10 minutes. After stirring for 30 minutes, the pH had fallen from above 11 to about 8 and after a further 2 hours the pH had fallen to about 7. The cooling bath was removed, 5.04 g (60 mmol) of solid sodium hydrogen carbonate were added and the mixture was stirred at room temperature overnight. The resulting suspension was filtered, the solid was dissolved in 90 ml of water and a small amount of insoluble material was removed by filtration. The combined filtrates were washed with two 150 ml portions of diethyl ether, stirred and cooled in an ice-bath and about 33 g of solid citric acid were added cautiously in order to adjust the pH to 3. The cold mixture was extracted with four 90 ml portions of diethyl ether, the combined extracts were filtered, dried over anhydrous sodium sulphate and evaporated to dryness at a temperature below 30° C. to give 10.5 g (98%) of D-α-tert.butoxycarbonylamino-1-tert.butoxycarbonyl-2-imidazolepropionic acid in the form of a colourless gum which crystallized on standing.

An ethereal solution of phenyldiazomethane (300 ml containing 4.18 g of phenyldiazomethane, 35.4 mol) was added dropwise while stirring over a period of 15 minutes to a suspension of 10.5 g (29.6 mmol) of D-α-tert.butoxycarbonylamino-1-tert.butoxycarbonyl-2-imidazolepropionic acid in 500 ml of diethyl ether. The mixture was stirred for 2 hours, the solid dissolving during the first hour, and was then left to stand at room temperature for 2 hours. The orange ethereal solution was shaken with 500 ml of 2M citric acid until the colour changed to pale yellow, washed with two 500 ml portions of 20% potassium carbonate solution and dried over sodium sulphate. Evaporation in vacuo gave 10.0 g (76%) of benzyl D-α-tert.butoxycarbonylamino-1-tert.butoxycarbonyl-2-imidazolepropionate in the form of a yellow oil.

Example 27

In an analogous manner to that described in Example 26(A), from benzyl L-α-tert.butoxycarbonylamino-1- tert.butoxycarbonyl-2-imidazolepropionate there was obtained benzyl L-α-amino-2-imidazolepropionate monohydrochloride of melting point 114°–117° C., $[\alpha]_D^{20} = +18.6°$ (c=0.996% in 1N hydrochloric acid).

Analysis for $C_{13}H_{15}N_3O_2 \cdot HCl$: Calculated: C: 55.4; H: 5.7; Cl: 12.6; N: 14.9%. Found: C: 55.3; H: 5.7; Cl: 12.7; N: 14.8%.

The benzyl L-α-tert.butoxycarbonylamino-1-tert-.butoxycarbonyl-2-imidazolepropionate used as the starting material was prepared from L-α-amino-2-imidazolepropionic acid in an analogous manner to that described in Example 26(B).

We claim:

1. A method for treating degenerative joint diseases or Wilson's disease which comprises administering to a host requiring the same an effective amount of a D- or L-compound of the formula

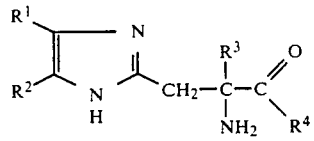

or a racemic mixture thereof wherein $R^1$, $R^2$ and $R^3$ each individually is hydrogen or lower alkyl and $R^4$ is hydroxy, lower alkoxy, lower alkoxy in which one of the hydrogen atoms has been replaced by unsubstituted phenyl or phenyl carrying one or more substituents selected from the group consisting of lower alkyl, lower alkoxy and halogen, amino, mono(lower alkyl)-amino or di(lower alkyl)amino, or a pharmaceutically acceptable salt thereof.

2. A method according to claim 1, wherein $R^1$, $R^2$ and $R^3$ each is hydrogen and $R^4$ is lower alkoxy containing at least 2 carbon atoms.

3. A method in accordance with claim 1, wherein the compound of formula I is ethyl D-α-amino-2-imidazolepropionate or a pharmaceutically acceptable salt thereof.

* * * * *